United States Patent [19]
Essman et al.

[11] Patent Number: 5,685,022
[45] Date of Patent: Nov. 11, 1997

[54] RENEWABLE EYE PROTECTIVE GOGGLE ASSEMBLY

[76] Inventors: David W. Essman, 212 Darrick Rd., Chaska, Minn. 55318; Jerry L. Winters, P.O. Box 784, Weleetka, Okla. 74880

[21] Appl. No.: 528,127

[22] Filed: Sep. 14, 1995

[51] Int. Cl.$^6$ ........................................ A61F 9/02
[52] U.S. Cl. ........................................ 2/434; 2/447
[58] Field of Search .................... 2/434, 432, 431, 2/440, 441, 443, 447, 426

[56] References Cited

U.S. PATENT DOCUMENTS

| | | | |
|---|---|---|---|
| 4,138,746 | 2/1979 | Bergmann | 2/434 X |
| 4,179,756 | 12/1979 | Lucas | 2/434 |
| 4,455,687 | 6/1984 | Johansson | 2/434 X |
| 4,455,689 | 6/1984 | Boyer | 2/434 |

FOREIGN PATENT DOCUMENTS 1136450  12/1956  France ........................................ 2/434

*Primary Examiner*—Peter Nerbun
*Attorney, Agent, or Firm*—Oliff & Berridge

[57] ABSTRACT

A goggle assembly is disclosed having a stacked array of disposable sheet members releasably held in position thereon by a plurality of flexible clamping members. Each of the clamping members is formed of a section of split rubber tubing secured to a lens support frame of the goggle. Each disposable sheet member has a manually engageable tab on one end thereof and an aperture formed in the other end. The aperture fits over a plastic hinge strap member held in position on a metal ventilator disc provided on one side of the goggle assembly.

22 Claims, 4 Drawing Sheets

RENEWABLE EYE PROTECTIVE GOGGLE ASSEMBLY

BACKGROUND OF THE INVENTION

The present invention is directed to a new improved and novel apparatus for providing eye protection for jockeys, skiers, snowmobilers and others who use goggles or the like which are subjected to the vision impairing accumulation of, snow, mud, or similar materials during use.

Jockeys, motorcycle riders, snowmobile drivers, skiers and others have employed goggles or similar devices for many years for eye protection. Regular goggle lenses frequently become covered and obscured by mud, snow or the like and consequently impair the vision of the user. Jockeys and other goggle users have consequently relied upon wearing a plurality of individual goggles sets, one of which is positioned over the eyes of the user and the others of which are maintained on the users riding helmet in an effort to alleviate the foregoing problem. Upon the accumulation of mud or other vision impairing material on the goggles being worn, the goggles are removed and clean goggles are placed in position over the users eyes. The foregoing procedure is awkward, distracting and time consuming and is therefore detrimental to the performance of jockeys and other users. This problem is particularly critical for jockeys since the loss of even a small fraction of a second in a race can negatively affect the finish order of a race. If clean goggles cannot be properly placed, the Jockey may effectively have to disengage from the pack of racing horses, losing all chance to achieve a high finish in the race.

Recognition of the shortcomings of using a plurality of goggles has resulted in a number of United States patents employing a plurality of stacked transparent flexible sheets held in position in front of the conventional goggle lens and being held so that the forwardmost transparent flexible sheet can be removed by the user when mud, snow or the like accumulates on its front surface to the extent that it impairs the users vision. Examples of the devices of the foregoing type include those found in U.S. Pat. Nos. 3,945,044; 4,076,373; 4,138,746; 4,455,687; 4,455,689; 4,563,065; and 4,716,601 all of which employ a plurality of transparent flexible sheets provided in stacked array in front of a primary lens of a goggle or the like with the sheets being arranged so that the forward sheet can be removed to enhance the vision of the user with the removed sheets then being discarded by the user. A common disadvantage of the devices disclosed in the foregoing patents is that the removed transparent flexible sheets are not retained on the user but are released by the user to trash and litter the surface of the area in which they are released. Even more significantly, when devices of the aforementioned type are used on a race track, the release of the removed sheet creates a safety hazard in that it could possibly engage the face of a trailing rider so as to create distraction or could conceivably distract and frighten a trailing horse which could bolt and cause injury to the other jockeys. Moreover, if a foreign object of the foregoing type is left on the track, trailing horses could slip upon such object causing a spill.

Another prior approach is shown in U.S. Pat. No. 4,179,756 in which a plurality of rigid lens are provided in front of the permanent lens of a pair of goggles in a rigid frame. This arrangement is overly heavy and clumsy to use and is particularly unsatisfactory for use by Jockeys.

Other prior known protective goggle arrangements employ a single removable shield in front of the main goggle lens with devices of this type being exemplified by U.S. Pat. Nos. 2,923,944; 3,056,140; 3,225357; 3,440,661 and 5,410,763.

Another approach to the solution of the problem of maintaining vision through goggles is found in U.S. Pat. Nos. 4,428,081 and 5,203,035 in which right and left rollers are provided on opposite sides of a goggle assembly and support a band of transparent material which is sequentially advanced in front of the permanent goggle lens as required to replace an obscured portion of the band with a clean portion. Devices of this type require excessive manual manipulation and have not achieved any substantial acceptance due to their difficulty of use and complexity.

Another proposed solution to the problem of maintaining clear vision through goggles is that illustrated in U.S. Pat. No. 5,107,543 which discloses a face mask on top of which a plurality of stacked light weight transparent goggle members are provided one on top of the other with each goggle member being retained in position by a strap extending around a rear portion of the users head. Devices of this type are obviously difficult to use and have not achieved any substantial acceptance.

Thus, there has remained a continuing unmet need for inexpensive, uncomplicated, easy to use and renewable eye protective goggles which will not create litter or a safety hazard and which will easily provide optimum clarity of vision for the user at a minimum of expense.

SUMMARY OF THE INVENTION

The preferred embodiment of the present invention comprises a conventional type goggle having a support frame which has been modified to permit the attachment of a stacked array of substantially transparent flexible of unbonded sheet members in the user view area in front of the permanent goggle lens to provide substantially unimpaired vision to the user. The stacked array of disposable sheet members is held in position on the goggle assembly by a plurality of flexible clamping members each formed of a section of split rubber tubing secured to the lens support frame of the goggle and operable for clampingly engaging the sheets of a stack of disposable transparent sheet members for retaining the stack on the goggle frame in the view area of the goggle. All of the disposable sheet members have a manually engageable tab on their left end (as viewed by the user) so that the forwardmost sheet member can be detached from the stack by hand engagement with its tab which is pulled forwardly to disengage the forwardmost sheet from the remaining sheets of the stack. However, the right end of each of the disposable sheets in the stack is provided with an aperture fitable over a hinge in the form of a flexible plastic hinge strap member bent into a U-shape and held in position on a metal ventilator disc provided on and part of the right side of the conventional goggle assembly. Upon disengagement of the forwardmost sheet from the stack it is released and the air stream flowing past the head of the user will swing the removed sheet rearwardly around the plastic hinge strip so that the removed sheet trails along the left side of the head of the user so as to avoid obscuring the vision of the user while also avoiding littering the race course or the other area on which the device is being used. Upon completion of the race or other activity in which the goggles are used, the sheets that have been removed from the stack can easily be removed from the goggle for proper disposal and replacement or possible refurbishing for further use if desired. In fact, the sheets can in some instances be rinsed off, permitted to dry and repositioned in stack array across the front of the goggle assembly without being removed from the assembly. The position of the manually engageable tabs can be reversed, depending on the desires of the user, so as to be on the right end rather than the left of the disposable sheet members.

DESCRIPTION OF THE PREFERRED EMBODIMENT

Figure 1:
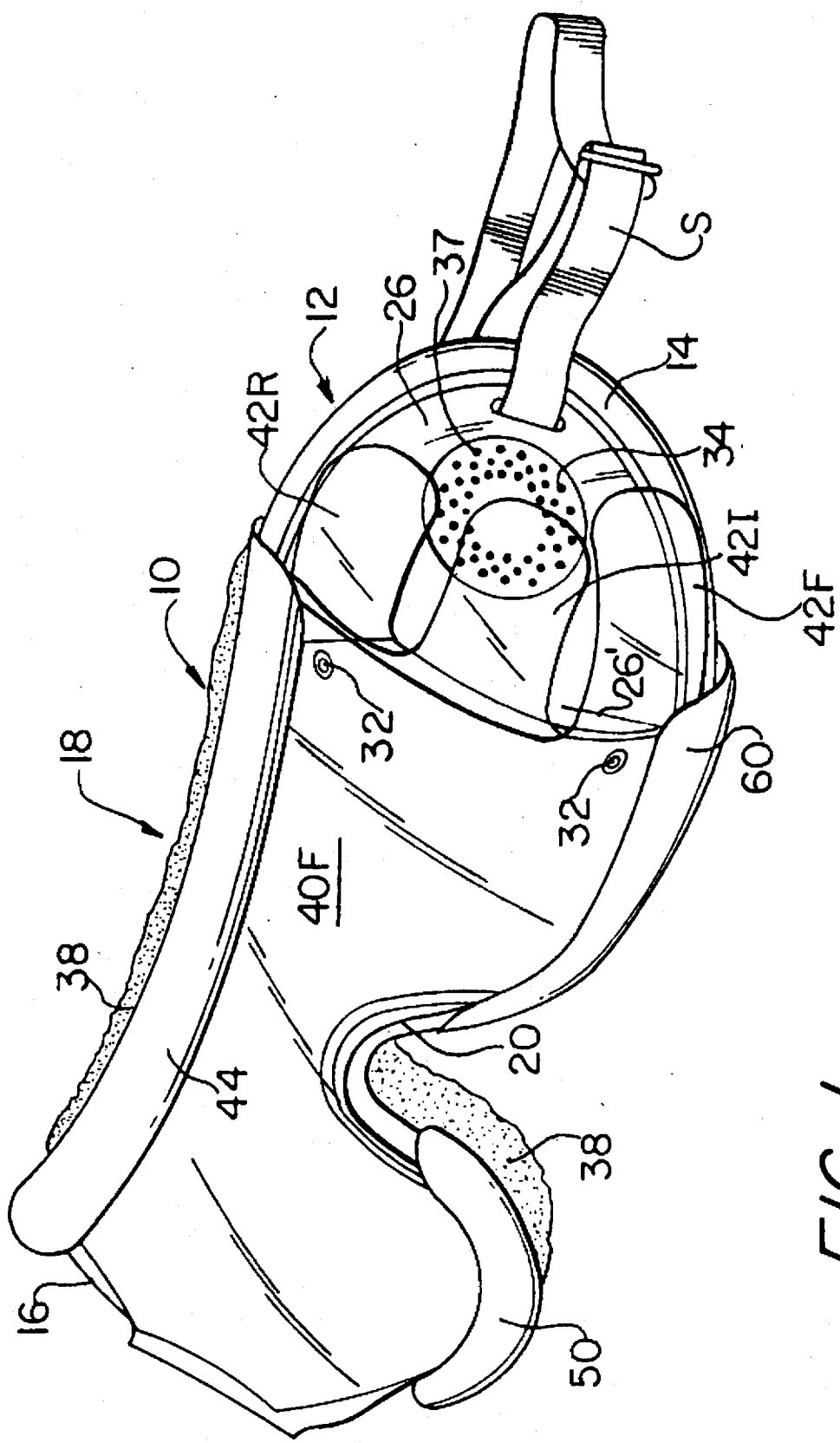
FIG. 1 is a perspective view of the preferred embodiment of the inventive goggle assembly as viewed from the forward left side of the user. It should be understood that the terms "right, left, forwardly, rearwardly" and equivalent terms are used in the sense of and with reference to, the person wearing the goggle assembly.
Figure 3:
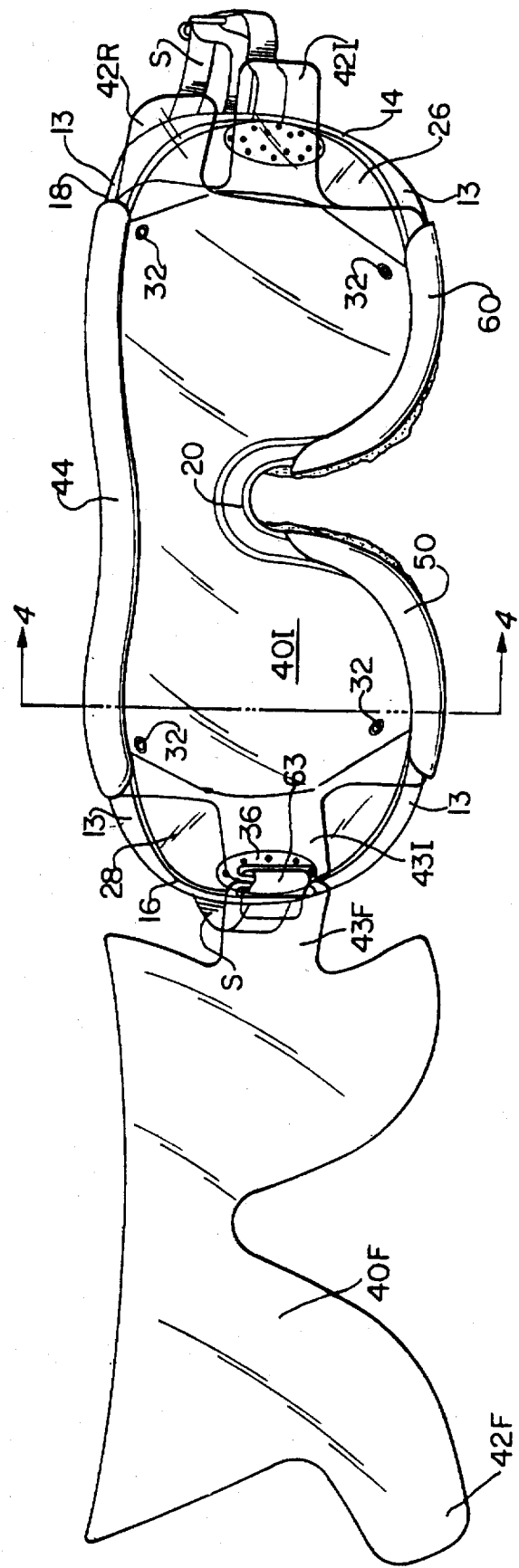
FIG. 3 is a front elevation of the preferred embodiment illustrating the manner in which one of the transparent sheets that has been removed from the stack is retained on the goggle.

Attention is initially invited to FIG. 1 of the drawings which illustrates the preferred embodiment of the invention, generally designated 10, which comprises a conventional goggle assembly such as that marketed by Kroop of Laurel Md. which has been modified so as to embody the invention. More specifically, a unitary closed loop goggle frame 12 having a left end portion 14 (FIG. 1), a right end portion 16, a generally horizontal upper portion 18 connecting the upper end of portions 14 and 16 and a central nose bridge portion 20 connecting the lower ends of end portions 14 and 16 provides support for the remaining components of the invention as shown in FIG. 3. Goggle frame 12 comprises the original conventional plastic goggle frame component 12' (FIG. 4) formed of plastic over the entire extent of which a plastic frame component 13 of generally U-shaped cross-section is fitted. Frame component 13 is not part of the conventional Kroop goggle assembly and need not necessarily be formed of plastic but can instead be formed of metal such as aluminum if desired.

A transparent permanent plastic lens 24 (FIG. 4) is mounted in goggle frame 12 in a conventional manner by a gasket 12" positioned in plastic goggle frame component 12'. The transparent permanent plastic lens 24 comprises a left temple facing component 26 and a right temple facing lens component 28 (FIG. 3) with a conventional main vision area lens component 30 being positioned between right and left temple facing components 26 and 28 in a well known manner. The left and right temple facing members 26 and 28 are respectively folded back along lines 26' and 28' to extend along the left and right temples of the user and are maintained in such orientation in well known conventional manner by rivets 32 extending through the main vision area 30 and through an inner edge portion of each of the temple facing lens components which is folded rearwardly on the side edge portions of the main vision area lens component 30.

A left ventilator disk 34 (FIG. 1) is mounted in the left temple facing component 26 and a right ventilator disc 36 (FIG. 2) is mounted in the right temple facing lens component 28. Both disks 34 and 36 are part of the conventional goggle means that is modified to achieve the present invention provided. Apertures 37 in each disk permit airflow into and out of the goggles to alleviate fogging of the interior of the main vision area 30 of the lens.

A foam cushion 38 is adhesively secured to the rear surface of the goggle frame 12 and extends about the entire peripheral extent thereof for providing comfort and safety for the user of the goggle assembly. A stacked array 39 of 10 mm MYLAR substantially transparent, flexible, unbonded and disposable sheet members is provided forwardly of the main vision area 30 of the permanent lens 24 and comprises a forwardmost substantially transparent flexible and disposable sheet 40F, an intermediate substantially transparent flexible sheet member 40I and rearmost substantially transparent sheet member 40F; additional transparent flexible sheets could be employed if desired. Forwardmost transparent and flexible sheet 40F is provided with a manually engageable stripper tab 42F on its left end which can be engaged by the hand of the user to remove the forwardmost sheet 40F from the face to the goggle assembly in a manner to be discussed. Similarly, the intermediate sheet 40I is provided with a stripper tab 42I and the rearmost sheet is similarly provided with a stripper tab 42R as shown in FIG. 1. It should be noted that the stripper tabs are not in horizontal alignment with each other so that they can be identified by feel and easily grasped by the user.

Figure 4:
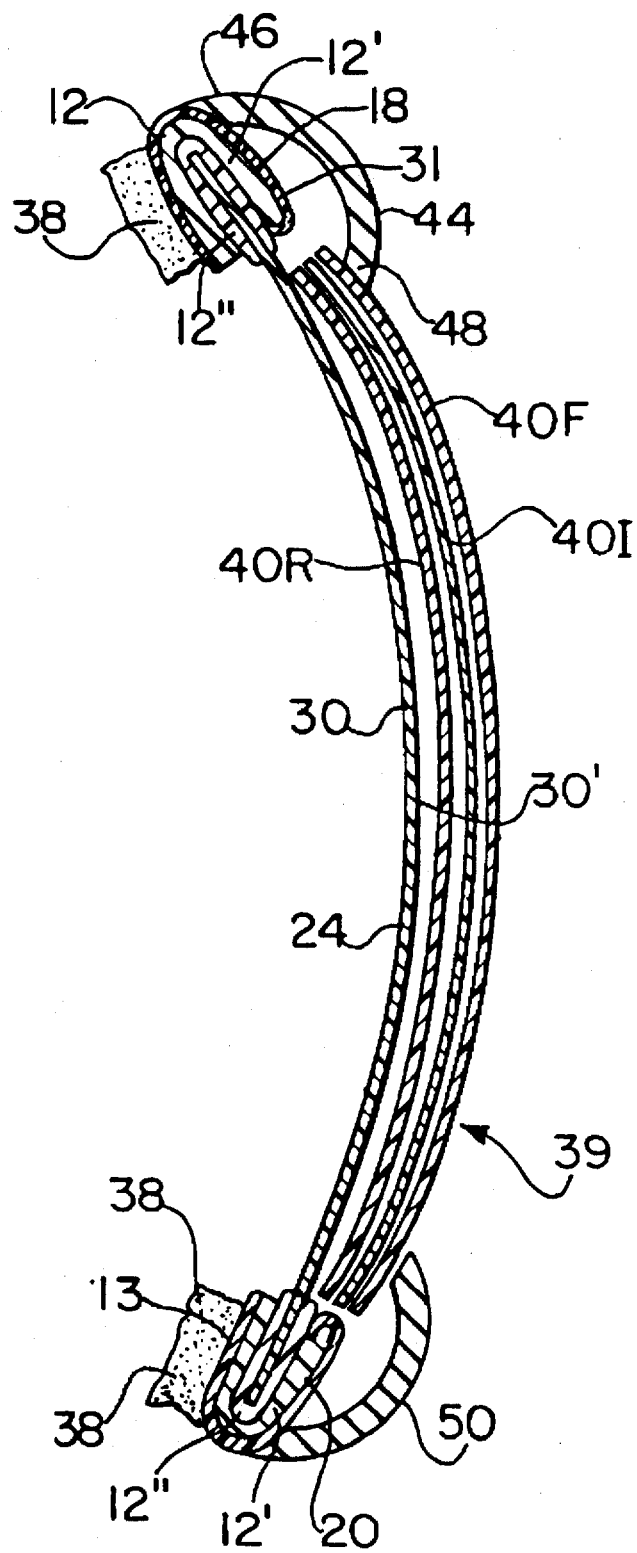
FIG. 4 is a sectional view taken along line 4—4 of FIG. 3.

Clamping means are provided for retaining the transparent sheets 40F, 40I and 40R in position on the goggle frame in front of the main view lens area 30. The clamping means includes an upper clamping member 44 formed of a section of resilient rubber tubing having a fixedly positioned edge portion 46 adhesively secured to upper portion 18 of the lens support goggle frame 12 as best shown in FIG. 4. Upper clamping member 44 also has a movable edge portion 48 which exerts force on the front surface of forwardmost sheet 40F to press the forwardmost sheet 40F rearwardly against intermediate sheet 40I which is itself pressed against rearmost sheet 40R which is consequently urged rearwardly against the main view area 30 of the lens component. Internal stress in the upper clamping member 44 creams the aforementioned force acting on the stack of sheets 40F, 40I, 40R. It should be understood that the aforementioned sheets and upper clamping member 44 are shown in a somewhat exploded manner in FIG. 4 to illustrate the positional relationship of the sheets whereas in actuality the three transparent sheets, 40F, 40I and 40R would be pressed against each other without there being any open space between the sheets. The upper portion of rearmost sheet 40R is pressed against the upper portion of forward face 30' of permanent lens 30 and held in position in an obvious manner.

Similarly, a lower right clamping member 50 and a lower left clamping member 60 are attached to the right and left portions of the central nose bridge portion 20 of frame 12 by adhesive means and are essentially identical in material, structure and function to the upper clamping member 44. Thus, the upper clamping member 44 and the two lower clamping members 50 and 60 serve to retain the stacked array of transparent sheet members 40F, 40I and 40R in position against forward face 30' of permanent lens 30.

Figure 2:
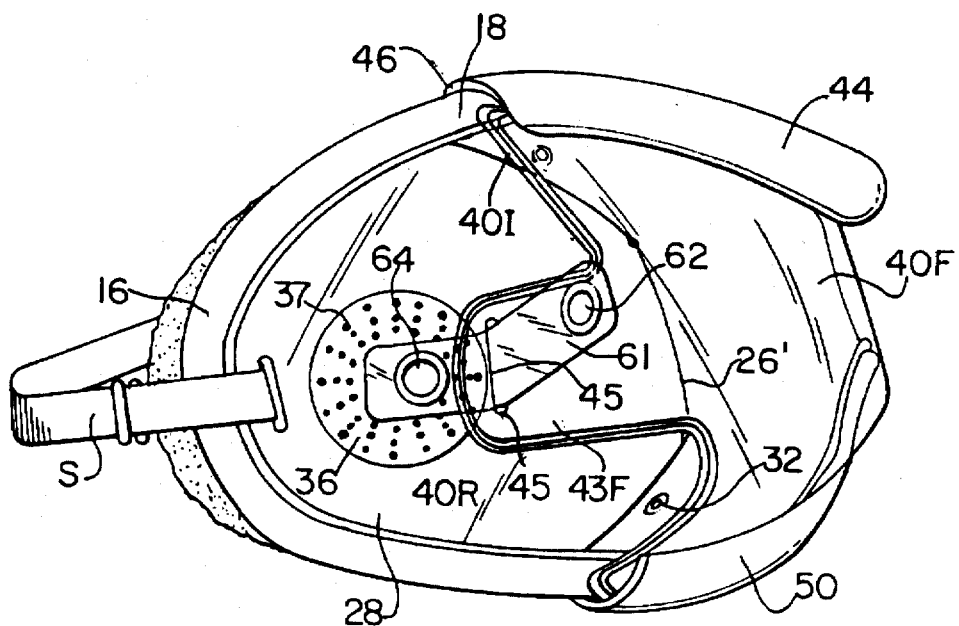
FIG. 2 is a right side elevation of the preferred embodiment.

The right ends of each of the transparent sheets members 40F, 40I, and 40R are all provided with identical mounting tabs 43F, 43I and 43R. The mounting tab 43F of the forwardmost transparent sheet 40F and the mounting tab 43I of intermediate transparent sheet 40I are both shown in FIG. 3. The mounting tab for the rearmost transparent sheet is not illustrated but is identical to the other two mounting tabs. Each mounting tab includes a hinge slot 45 positioned over a flexible plastic hinge strap 61 in which a female snap connector 62 is mounted. A male snap connector 64 attaches the opposite end of strap 60 to the right ventilator disk 36 as best shown in FIG. 2. Plastic hinge strap 61 is in the sheet loading open position with snap connectors 62 and 64 being unconnected as shown in FIG. 2 at the time the goggle assembly is provided with the stacked array of transparent sheets 40F, 40I, and 40R being in position so that their slots 45 fit over the plastic hinge strap 61 and the clamp members 44, 50 and 60 engage the upper and lower edges of flexible sheet 40F to hold it and sheets 40I and 40R in position. Plastic hinge strap 61 is then bent rearwardly so that a female snap connector 62 is snappingly engaged with the male snap connector 64 to provide a hinge loop 63 in which the mounting tabs 43F, 44I and 43R are loosely held.

Figure 5:
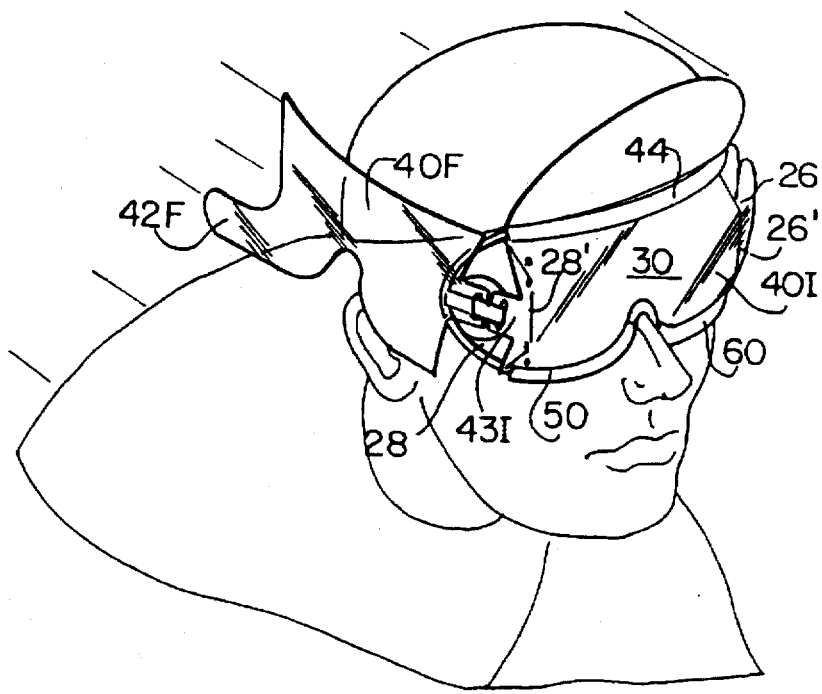
FIG. 5 is a perspective view of the preferred embodiment in use showing a previously removed sheet member trailing alongside the user's head.

The entire assembly is maintained on the user's head in a well known manner by means of a headstrap S and when the forwardmost sheet 40F receives a covering of mud, dirt, snow or other vision impairing material the user grasps the stripper tab 42F and pulls forwardly and to the right to strip the forwardmost sheet 40F from the clamping members 44, 50 and 60 so that the forwardmost sheet moves to and through the position shown in FIG. 3 to the FIG. 5 trailing position extending along side the right side of the user's head. The rearwardly moving air stream maintains the removed previously forwardmost sheet 40F in the illustrated trailing position along side the user's head so that it does not interfere with his vision as shown in FIG. 5. Moreover, the hinge loop 63 of plastic strap 61 holds the removed transparent sheet on the goggle assembly and prevents it from escaping to create litter or possible danger if the device is being used in competitive events such as horse racing.

If the intermediate sheet 40I (which has become the forwardmost sheet) then becomes impaired by the deposit of mud, or the like, it can then be stripped forwardly and to the right in the same manner as sheet 40F to expose the rearmost sheet 40R. All stripped sheets are retained on the goggle by the operation of the hinge strap 61 in an obvious manner as shown in FIG. 5.

When the use of the goggle assembly is completed, the hinge snap connectors 62 and 64 can be disconnected so that the trailing flexible transparent sheets can be removed, discarded and replaced with new transparent sheets. However, in some instances it would be practical to simply clean the removed transparent sheets and remount them on the goggle assembly. Moreover, the soiled sheets can be cleaned by a water spray while still positioned on the hinge strap 61, then permitted to dry and repositioned across the front of the goggle assembly in the manner shown in FIG. 1 so as to be ready for subsequent use.

Numerous modifications of the disclosed embodiment will undoubtedly occur to those of skill in the art. For example, the goggle frame 12 need not be based on a "Kroop" frame and could be formed of a unitary single piece of molded plastic; thus, it is not essential that a conventional goggle assembly be employed as a basic support structure in order to practice the invention. Similarly, different types of retaining means for holding the stacked array of transfer sheets on the goggle frame can also be employed. In like manner, the clamping means for retaining the stack in position on the goggle assembly can be formed of resilient material other than rubber if desired. Thus, it is essential that it be understood that the scope of the invention is not limited to the disclosed structure but is limited solely by the following claims.

We claim:

1. An eye protective apparatus comprising:

a goggle type lens support frame mountable on the head of a user for positioning a user view area forwardly of the user's eyes;

a stacked array of substantially transparent, flexible and unbonded and disposable sheet members in the user view area through which the user can have substantially unimpeded vision, said stacked array of substantially transparent sheet members having first and second side edge portions and including a rearmost transparent sheet member facing and closest to the user's eyes and a forwardmost transparent sheet member positioned forwardly of the rearmost transparent sheet member with all of the sheets of said stacked array having upper and lower edges and right and left side edges;

clamping means mounted on said support frame for engaging said forwardmost sheet member and urging the forwardmost sheet member rearwardly to urge the rearmost sheet member toward the lens support frame for removably holding said stacked array of substantially transparent sheets in position in the user view area;

manually engageable tab means on one of said side edges of the sheets of said stacked array of said substantially transparent sheets positioned to be engageable by a hand of the user for forward movement resultant in said forwardmost sheet being pulled from and disengaged from said clamping means and removed from the user's view area to expose the next sheet immediately to the rear of the removed sheet so that the next sheet then becomes the forwardmost sheet;

said clamping means comprising hose sector means having at least one lengthwise extending transparent sheet engaging edge comprising a clamp edge engaged with said forwardmost sheet for urging said forwardmost sheet rearwardly;

said hose sector means being made of a rubber-like material and including a second lengthwise extending edge secured to said lens support frame;

said hose sector means comprising upper hose sector means mounted on an upper horizontal user brow facing frame component positioned above the user view area and lower hose sector means mounted on lower transverse frame component means of said lens support frame positioned below the user's view area;

said lower hose sector means comprising right lower hose sector means and left lower hose sector means respectively mounted to the right and to the left of a nose bridge component of said lower transverse frame component;

each of said hose sector means comprising a lengthwise extending generally arcuate sector in cross-section bounded on one side by said second lengthwise extending edge fixedly attached to said lens support frame and said clamp edge that clampingly engages the front surface of said forwardmost sheet member; and a generally vertical hinge connection between said first side edge portion of each of said transparent sheets of said stacked array and said first side portion of said lens support frame adjacent thereto so that said removed sheet can pivot about a generally vertical axis to assume a rearwardly trailing retained position relative to said hinge connection in response to windflow in a rearward direction relative to the user.

2. The eye protective apparatus of claim 1 wherein said hinge connection comprises a strap loop fixedly positioned relative to said lens support frame and loosely passing through a generally vertical slot in the first side edge portion of each of said transparent sheets so that each of said transparent sheets is pivotable about said strap loop.

3. The eye protective apparatus of claim 2 additionally including a permanently mounted plastic lens body mounted on said lens support frame rearwardly of and adjacent said rearmost sheet and having a generally transverse view portion forwardly of and aligned with and facing the user's eyes and rearwardly trailing temple facing portions at least one of which has an apertured ventilation disk mounted therein.

4. The eye protection apparatus of claim 3 wherein said strap loop is mounted on said apertured ventilation disk by a male/female snap connector formed of a male snap component and a female snap component, one of said snap components being mounted on said ventilation disk for clamping one end of said strap loop thereto and the other snap component being mounted on an opposite end of said strap loop for connection to said one of said snap components to form and maintain said strap loop in position on said ventilation disk.

5. An eye protective apparatus comprising:

a goggle type lens support frame mountable on the head of a user for positioning a user view area forwardly of the user's eyes;

a stacked array of substantially transparent, flexible and unbonded and disposable sheet members in the user view area through which the user can have substantially unimpeded vision, said stacked array of substantially transparent sheet members having first and second side edge portions and including a rearmost transparent sheet member facing and closest to the user's eyes and a forwardmost transparent sheet member positioned forwardly of the rearmost transparent sheet member with all of the sheets of said stacked array having upper and lower edges and right and left side edges;

clamping means mounted on said support frame for engaging said forwardmost sheet member and urging the forwardmost sheet member rearwardly to urge the rearmost sheet member toward the lens support frame for removably holding said stacked array of substantially transparent sheets in position in the user view area;

manually engageable tab means on one of said side edges of the sheets of said stacked array of said substantially transparent sheets positioned to be engageable by a hand of the user for forward movement resultant in said forwardmost sheet being pulled from and disengaged from said clamping means and removed from the user's view area to expose the next sheet immediately to the rear of the removed sheet so that the next sheet then becomes the forwardmost sheet; and a permanently mounted plastic lens body mounted on said lens support frame rearwardly of and adjacent said rearmost sheet and having a generally transverse view portion forwardly of and aligned with and facing the user's eyes and rearwardly trailing temple facing portions at least one of which has an apertured ventilation disk mounted therein.

6. The eye protective apparatus of claim 5 wherein said clamping means comprises hose sector means.

7. The eye protective apparatus of claim 6 wherein said hose sector means is made of rubber-like material.

8. The eye protective apparatus of claim 7 wherein said hose sector means comprises upper hose section means mounted on an upper horizontal user brow facing frame component of said lens support frame positioned above the user view area and lower hose sector means mounted on lower transverse frame component means of said lens support frame positioned below the users view area.

9. The eye protective apparatus of claim 8 wherein said lower hose sector means comprises right hose sector means and left hose sector means respectively mounted to the right and to the left of a nose bridge component of said lower transverse frame component.

10. The eye protective apparatus of claim 9 wherein each of said hose sector means comprises a lengthwise extending generally arcuate sector in cross-section bounded on one side by an attachment edge fixedly attached to a lens supporting frame component and a movable clamp edge that clampingly engages the front surface of said forwardmost sheet member.

11. The eye protective apparatus of claim 10 additionally including a generally vertical hinge connection between first side edge of each of said transparent sheets of said stacked array and a side portion of said lens support frame adjacent said first side edge so that said removed sheet can pivot about a generally vertical axis to assume a rearwardly trailing position relative to said hinge connection in response to windflow in a rearward direction relative to the user.

12. The eye protective means of claim 11 wherein said hinge connection comprises a strap loop fixedly by positioned relative to said lens support frame and loosely passing through a generally vertical slot in the first side edge portion of each of said transparent sheets so that each of said transparent sheets is pivotable about said strap loop.

13. An eye protective apparatus as recited in claim 5 additionally including a hinge tab extending outwardly of the first side edge portion of each of said transparent sheets, a generally vertical hinge connection between one of said temple of facing portions said lens support frame and said hinge tab so that said removed sheet can pivot into a rearwardly trailing position relative to said hinge connection in response to rearward windflow past the user.

14. The eye protective apparatus of claim 13 wherein said clamping means comprises hose sector means.

15. The eye protective apparatus of claim 14 wherein said hose sector means is made of rubber-like material.

16. The eye protective apparatus of claim 15 wherein said hose sector means comprises upper hose sector means mounted on an upper horizontal user brow facing frame component of said lens support frame positioned above the user view area and lower hose sector means mounted on lower transverse frame component means of said lens support frame positioned below the users view area.

17. The eye protective apparatus of claim 16 wherein said lower hose sector means comprises right hose sector means and left hose sector means respectively mounted to the right and to the left of a nose bridge component of said lower transverse frame component.

18. The eye protective apparatus of claim 17 wherein each of said hose sector means comprises a lengthwise extending generally arcuate sector in cross-section bounded on one side by an attachment edge fixedly attached to its supporting frame component and a movable clamp edge that clampingly engages the front surface of said forwardmost sheet member.

19. An eye protective apparatus comprising:

a goggle type lens support frame mountable on the head of a user for positioning a user view area forwardly of the user's eyes;

a stacked array of substantially transparent, flexible and unbonded and disposable sheet members in the user view area through which the user can have substantially unimpeded vision, said stacked array of substantially transparent sheet members having first and second side edge portions and including a rearmost transparent sheet member facing and closest to the user's eyes and a forwardmost transparent sheet member positioned forwardly of the rearmost transparent sheet member with all of the sheets of said stacked array having upper and lower edges and right and left side edges;

clamping means mounted on said support frame for engaging said forwardmost sheet member and urging the forwardmost sheet member rearwardly to urge the rearmost sheet member toward the lens support frame for removably holding said stacked array of substantially transparent sheets in position in the user view area;

manually engageable tab means on one of said side edges of the sheets of said stacked array of said substantially transparent sheets positioned to be engageable by a hand of the user for forward movement resultant in said forwardmost sheet being pulled from and disengaged from said clamping means and removed from the user's view area to expose the next sheet immediately to the rear of the removed sheet so that the next sheet then becomes the forwardmost sheet;

at least one intermediate transparent sheet being positioned between said rearmost sheet member and said forwardmost transparent sheet;

said clamping means comprising hose sector means;

said hose sector means being made of rubber-like material;

said hose sector means comprising upper hose sector means mounted on an upper horizontal user brow facing frame component of said lens support frame positioned above the user view area and lower hose sector means mounted on lower transverse frame component means of said lens support frame positioned below the user's view area;

said lower hose sector means comprising right hose sector means and left hose sector means respectively mounted to the right and to the left of a nose bridge component of said lower transverse frame component of said lens support frame;

each of said hose sector means comprising a lengthwise extending generally arcuate sector in cross-section bounded on one side by an attachment edge fixedly attached to its supporting frame component and a movable clamp edge that clampingly engages the front surface of said forwardmost sheet member; and a generally vertical hinge connection between the other side edge of each of said transparent sheets of said stacked array and a side portion of said lens support frame adjacent said other side edge so that said removed sheet can pivot about a generally vertical axis to assure a rearwardly trailing position relative to said hinge connection in response to windflow in a rearward direction relative to the user.

20. The eye protector of claim 19 wherein said hinge connection comprises a strap loop fixed by positioned relative to said lens support frame and loosely passing through a generally vertical slot in the first side edge portion of each of said transparent sheets so that each of said transparent sheets is pivotable about said strap loop.

21. The eye protective apparatus of claim 20 additionally including a permanently mounted plastic lens body mounted on said lens support frame rearwardly of and adjacent said rearmost sheet and having a generally transverse view portion forwardly of and aligned with and facing the user's eyes and rearwardly trailing temple facing portions at least one of which has an apertured ventilation disk mounted therein.

22. The eye protection apparatus of claim 20 wherein said strap loop is mounted on said apertured ventilation disk by a male/female snap connector formed of a male snap component and a female snap component, one of said snap components being mounted on said ventilation disk for clamping one end of said strap loop thereto and the other snap component being mounted on an opposite end of said strap for connection to said one of said snap components to form and maintain said strap loop in position on said ventilation disk.

* * * * *